United States Patent [19]
Testa

[11] Patent Number: 5,866,179
[45] Date of Patent: Feb. 2, 1999

[54] MEDICATED CHEWING GUM AND A PROCESS FOR PREPARATION THEREOF

[75] Inventor: Emilio Stefano Testa, Chiasso-Vacallo, Switzerland

[73] Assignee: Avant-Garde Technologies & Products S.A., Chiasso-Vacallo, Switzerland

[21] Appl. No.: 646,744

[22] Filed: May 3, 1996

[51] Int. Cl.$^6$ .................................................. A23G 3/30
[52] U.S. Cl. .............................. 426/3; 426/531; 424/440; 424/441; 424/464; 424/195.1; 514/343; 514/836
[58] Field of Search ................................. 424/441, 195.1, 424/440, 464, 484; 426/3, 531; 514/343, 836

[56] References Cited

U.S. PATENT DOCUMENTS

| | | |
|---|---|---|
| 3,262,784 | 7/1966 | Bucher . |
| 4,068,004 | 1/1978 | Carlin et al. . |
| 4,161,546 | 7/1979 | Akin et al. . |
| 4,348,416 | 9/1982 | Boden . |
| 4,849,225 | 7/1989 | Mitsuhashi et al. . |
| 4,882,176 | 11/1989 | Koyama et al. . |
| 5,165,943 | 11/1992 | Patel et al. . |
| 5,229,148 | 7/1993 | Copper . |
| 5,314,877 | 5/1994 | Suzuki et al. . |
| 5,344,659 | 9/1994 | Kurihara et al. . |
| 5,362,496 | 11/1994 | Baker et al. . |
| 5,370,881 | 12/1994 | Fuisz . |

FOREIGN PATENT DOCUMENTS

| | | |
|---|---|---|
| 0 151 344 A2 | 8/1985 | European Pat. Off. . |
| 0 575 977 A2 | 12/1993 | European Pat. Off. . |

*Primary Examiner*—Raj Bawa
*Attorney, Agent, or Firm*—Darby & Darby

[57] ABSTRACT

The present invention relates to a medicated chewing gum comprising a pharmaceutically active agent incorporated therein. The medicated gum is used as a means for administering the active agent to a subject. The invention also relates to a method of preparing the medicated chewing gum. The process involves the formation of a cyclodextrin-active agent inclusion complex, which is dried and mixed with a granulated gum base without adding water or other solvents. The process is carried out under controlled temperature and humidity and the blended components are cold-pressed to produce a final gum product.

44 Claims, No Drawings

MEDICATED CHEWING GUM AND A PROCESS FOR PREPARATION THEREOF

The present invention relates to a process for the preparation of medicated chewing gum containing a pharmaceutically active agent for instant release. The gum has a pleasant taste, regardless of any unpleasant organoleptic characteristics of the active agent. The novel process employed in the present invention is carried out in the absence of added organic solvents and water and under controlled temperature and humidity to protect sensitive active agents from degradation.

BACKGROUND OF THE INVENTION

Attempts have long been made to incorporate pharmaceutically active agents into chewing gum as a means of administering the active agent to the subject. Traditionally, these efforts have employed common chewing gum production techniques wherein a gum base is heated until it becomes a viscous or fluid mass. Additional components (such as flavors or active ingredients) then blended into the gum base. Finally, the mixture is cooled, pressed and cut to produce the final product.

Alternatively, the various components are blended in a gum slurry that is coagulated before pressing into the final product form.

However, many pharmaceutically active agents possess unpleasant taste or odor characteristics which were all too apparent when mixing with gum by the above method, resulting in undesirable chewing gum products. Many active agents also tend to irritate the mucosas. Still other pharmaceutically active agents degrade rapidly, making it impractical to include them in chewing gum.

Another problem with known methods is that the gum base is heated to a fluid mass to facilitate mixing of other ingredients. Such elevated temperatures can cause degradation of heat-sensitive compounds, including active agents and flavors.

Prior art attempts to overcome these difficulties included the following: to avoid the degradation of the active agents, chewing gum was cold-produced by direct compression of the ingredients; to obtain the ability to retard or control the release rate of active agents, the active agents were formulated into microcapsules. However, microencapsulation technology is complex and costly often resulting in retarded release products. It is therefore not well-adapted for drugs for which rapid absorption through the oral mucosas is necessary or desirable.

In addition, known processes for medicated gum preparations often utilize organic solvents to dissolve the active agents. It is well known that these organic solvents are difficult to eliminate from the final product and may present certain health risks if even trace amounts remain in the final dosage form. Additionally, use of organic solvents in connection with industrial processes is becoming increasingly unpopular due to health and environmental considerations (e.g., risks attendant to exposure of personnel and problems in effecting proper disposal of waste solvents).

Water has also been utilized in gum preparations, but it is difficult to eliminate, especially at the relatively low temperatures that are desirable for production of chewing gum. Heating the gum mass to eliminate water is not advisable, because the gum will then become more sticky which makes handling difficult and interferes with large-scale, semi- or totally automated production.

Thus, the problems of realizing a medicated chewing gum produced by direct compression, with immediate or rapid release of the active agent and efficient masking of unpleasant organoleptic characteristics of active agents, remained unsolved.

The properties of cyclodextrin in forming inclusion complexes have been recognized and some of the difficulties recounted above were solved by applying these techniques. It was found that certain compounds could be included within cyclodextrins and then blended into a gum base under traditional chewing gum production methods. The compounds were then released upon chewing. See, for example, U.S. Pat. No. 5,165,943 to Patel et al.

Although these methods helped to mask the unpleasant taste of certain compounds and reduce degradation, there were still significant shortcomings. Water and stickiness are still problems, and the methods known in the art do not address the temperature sensitivity of certain active agents.

SUMMARY OF THE INVENTION

In view of the deficiencies of the prior methods of producing medicated chewing gum containing active agents, the present process was developed to overcome these various shortcomings and provide a novel process for producing medicated chewing gum containing inclusion complexes of cyclodextrin-enclosed active agents.

This process avoids the use of organic solvents and water and is especially adapted for use with heat-sensitive active agents. Further, the process of this invention avoids the heated gum base and gum slurries previously known in the art.

These objectives and others are accomplished by cooling the gum base grinding it into granules which are then dry-mixed with optional excipients in the absence of water and solvents at controlled temperature and humidity. These objectives are further achieved by cold-pressing the mixed gum and components into the final tablet form.

DETAILED DESCRIPTION OF THE INVENTION

The present invention relates to a process for the preparation of medicated chewing gum containing inclusion complexes of cyclodextrin-enclosed active agent in which the components are dry-mixed under controlled temperature and humidity and the resulting gum blend is cold-pressed under similar controlled temperature and humidity. As used herein "medicated" chewing gum means chewing gum containing one or more of the following active agents: a physiologically active ingredient, nutritional supplement or pharmaceutically active ingredient. Non-limiting examples of active agents are given below.

Cyclodextrins are α-1,4-cyclic maltoligosaccharides having six to twelve glucose units. Branched cyclodextrins with glucose units connected by α-1,6-glucosidic bonds also exist.

The cyclodextrins are formed enzymatically from starch through the action of the glycosyl transferase produced by certain microorganisms. β-cyclodextrin, having seven glucose units and a molecular weight of 1135, is preferred for use in the present invention. Cyclodextrin preparation is well-known in the art. The commercially-available, colorless, crystalline form of β-cyclodextrin with purity greater than 98% is most preferred.

Active agents suitable for use in the medicated chewing gum disclosed herein include, but are not limited to vitamins, and particularly l-ascorbic acid (Vitamin C); analgesics, and particularly acetaminophen (APAP) and ibuprofen; antihistamines; and particularly dimenhydrinate; antibacterial agents, and particularly chlorhexidine diacetate; chelated minerals, and particularly chromopoly picolinate; tonic agents, and particularly ginseng; circulatory agents, and particularly ginkgo biloba extracts; oral deodorants, and particularly tea and vegetable extracts; and nicotine.

The hydrosoluble and liposoluble active agents are encapsulated within cyclodextrins and are liberated in the mouth by saliva amylases. By inclusion in cyclodextrins, the active agents are stabilized and are made more soluble. The well-developed technology used for generating the inclusion complexes is simpler and advantageous relative to the techniques necessary for micro-encapsulation.

Furthermore, through the use of the inclusion complexes, the bioavailability of the cyclodextrin-encapsulated active agents is accentuated. In addition, this technique provides an excellent means of masking the unpleasant organoleptic characteristics of many active agents. Further details are provided in Italian Patent Application MI 95/A 000180 to Testa et al, filed Feb. 2, 1995, the disclosure of which is incorporated by reference in its entirety (in case of conflict, the present specification controls).

The process for the preparation of the medicated chewing gum is described below in its general embodiment by way of example. However, it is possible to effect numerous alternative variations, as will be clear to one of ordinary skill in the art.

The inclusion complex can be prepared by a variety of means familiar to one skilled in the art. Typically, a quantity of cyclodextrin is placed in an appropriate container with an appropriate amount, e.g., 1 to 2 parts, distilled water. The suspension is mixed, e.g., with a mechanical stirrer, for 10–15 minutes until complete homogenization. Then an equivalent amount of active agent is added (sufficient to be included in cyclodextrin inclusion complexes). After the active agent is added, the suspension is mixed for the amount of time necessary to complete the inclusion of active agent in the cyclodextrin, usually from 3 to 5 hours.

The inclusion complex suspension is then dried. Water can be removed from the mix under vacuum, or this can also be accomplished through the use of a rotating shaker or in an oven, where a temperature of less than 50° C. is maintained. The resulting solid is ground until it passes 50–500 mesh, resulting in a dried powdered form of inclusion complex. The inclusion complex is eventually added to the gum base after the gum base has been processed as explained below.

The gum base used in the present invention may be any suitable gum base known in the art, including natural gum such as chicle, jelutong, gutta percha and crown gum.

The gum base is prepared by cooling natural gum to $-10°$ C. and grinding it. Guar gum and glycerine are preferably added such that the resulting gum blend typically comprises a ratio of 99 to 0.9 to 0.1 by weight (natural gum:guar gum:glycerine).

One or more well known chewing gum excipients can be added to the gum base, before or after combining it with the inclusion complex. These excipients include, but are not limited to, sweeteners, flavoring agents, and compression adjuvants.

Sweeteners are generally carbohydrates, particularly sucrose and glucose. If non-cavity generating products are desired, mannitol, sorbitol, glycine and other non-cavity generating excipients may be used. For such non-cavity generating products, sweeteners such as aspartame, cyclohexyl sulfamate, saccharine, acesulfame k, stevioside, and ammonium glycyrrhizinate may be used.

Flavoring agents may also be added to the gum base. Flavoring agents suitable for use in the present invention include, but are not limited to, essential oils and synthetic flavors such as citrus oils, fruit essences, peppermint oil, spearmint oil, clove oil, oil or wintergreen, anise and the like. Artificial flavorants known to those skilled in the art are also contemplated by this invention.

Compression adjuvants may also be added. These compounds facilitate compression of the gum into tablets. Suitable compression adjuvants include, but are limited to, silicon dioxide, magnesium stearate, calcium stearate, behenic acid, talc and similar substances can be used, and are often essential, to limit the tendency of the gum tablets to stick to the presses.

The powder containing the inclusion complexes of cyclodextrin and active agent is then mixed with the processed gum base in the absence of water or organic solvents. The ratio between the inclusion complex and the processed gum base can vary widely (depending on the amount of active agent that should be delivered per gum tablet), the following range (by weight) being useful for most applications:

$$\frac{110}{650} \leq \frac{\text{inclusion complex}}{\text{processed gum base}} \leq \frac{150}{65}$$

The process of the present invention is improved by maintaining controlled temperature and humidity. The mixture of the other components with the gum base is carried out at a temperature below 20° C., preferably below 18° C., and at relative humidity below 50%. It should be noted that the temperature should not be so low as to interfere with the handling of the medicated gum and the tableting process. Thus, preferably, the temperature should be above 10°–12° C.

The final mixture is then transferred to a suitable tableting machine for production of the final chewing gum product. The tableting machine is also kept at temperatures below 20° C. and preferably below 18° C., and the relative ambient humidity is maintained below 50% but typically at 40% or above (always below 50%). By way of example, an 18 punch machine, such as the Ronchi RD18, (Fratelli RONCHI S.p.A., Cinsello Balsamo, Italy) can produce 50,000 units/hour by the above-described method.

The final tablets typically weigh between 1.5–3.5 g and when chewed, they form a gummy clot without any unpleasant taste or irritation to the mucosas.

The process according to the present invention is further described in the following examples, which are provided purely by way of illustration and are not meant to limit the scope of the invention in any way.

EXAMPLES

Example No. 1

A slurry of 135 g of β-cyclodextrine and 20 g of l-ascorbic acid (vitamin C) in 300 ml of distilled water are placed in a glass flask provided with a mechanical stirrer and mixed for 5 hours at room temperature (15°–25° C.). After stirring, vacuum is applied (10–30 mm Hg) and the water is removed by heating progressively up to 50° C. The dry product obtained is sieved through 50 mesh.

A portion of this product—140.5 g—is mixed with 68 g of dry (solvent-free) gum base previously prepared as follows: natural gum is cooled to −10° C., ground and diluted with 0.9% guar gum and 0.1% glycerine (w/w). The whole is sieved through 50 mesh. The obtained blend totals 208.5 grams.

Two g of mannitol, 2 g of glycocoll, 3 g of syloid 244 (GRACE G.m.b.H. D-67545 Worms in der Hollanbacke) and 1 g of behenic acid are added. The whole (216 g) is mixed for 15 minutes and sieved through 200 mesh. Lastly, 3 g of aspartame (artificial sweetener), 5.5 g of orange oil and 1 g of magnesium stearate (compression adjuvant) are added. From this is obtained 226 g of granules that are compressed on a RONCHI R18 rotary press. Ninety tablets are obtained. Weight of the tablets: 2.5 g. Each tablet contains 200 mg of vitamin C.

Example No. 2

A slurry of 105 g of cyclodextrin and 15 g of acetaminophen (APAP) in 250 ml of distilled water is prepared in a glass flask provided with a mechanical stirrer and mixed for three hours at 25° C. After this time, vacuum is applied (15–20 mmHg) and the water is removed by heating progressively up to 50° C. (bath temperature). The product obtained is sieved through 50 mesh.

A part of this product, 108 g., is mixed with 72 g of gum base itself prepared by cooling the gum base (Jelutong) to −10° C., grinding it, then adding 0.9% of guar gum and 0.1% glycerine (w/w). The whole is sieved through 50 mesh. The final blend totals 180 g.

5 g of sucrose, 3 g of syloid 244 and 1 g of behenic acid are added to the gum base. The whole is mixed in a tumbler (class K mixer) at a temperature less than 20° C. Lastly, 5 g of aspartame, 3.5 g of grapefruit scent and 1 gram of magnesium stearate are added. The components are mixed in a tumbler for 5 minutes and sieved through 50 mesh. 226 g of granules are obtained and compressed on a RONCHI rotary press obtaining 90 tablets (theoretical yield). Weight of the tablets: 2.5 g with a content of 150 mg of APAP (median weight).

Example No. 3

A slurry is prepared of 140 g of β-cyclodextrine and 20.6 g of ibuprofen in 200 ml of distilled water: the blend is stirred for 5 hours at 20° C. (room temperature). The slurry is transferred to a glass tray, placed in a vacuum dryer and heated to 50° C. Theoretical yield: 161 g.

144.9 g are taken out and mixed with 75.1 g of gum base prepared by cooling the natural gum (Jelutong) to −10° C., grinding in a mechanical mill, and adding 0.9% of guar gum and 0.1% glycerine (w/w). The gum-base components are mixed in a tumbler and passed through a sieve at 50 mesh. The final blend weighs 220 g. To the blend is added 5 g of mannitol, 4 g of syloid 244 and 1 g of behenic acid. This is mixed in a tumbler for 20 minutes at a temperature less than 20° C. Lastly, in the same tumbler 10 g of aspartame, 7.5 g of mint scent and 2.5 g of magnesium stearate are added. The blend is mixed for 5 minutes, passed through a sieve (50 mesh) and the final granules (249 g) are compressed on a rotary press. From this, 90 tablets (theoretically) of a weight of 2.750 g, containing 200 mg of ibuprofen, are obtained.

Example No. 4

A slurry is prepared comprised of 100 g of β-cyclodextrines and 25 g of dimenhydrinate (antihistaminic product) in 150 ml of distilled water: the blend is stirred for 5 hours at 20° C. (room temperature). The slurry is transferred to a glass tray, placed in a vacuum dryer and dried to 50° C. until a total evaporation of the water occurs (constant weight). The granules are sieved through 50 mesh. Theoretical yield: 125 g.

114.5 g are taken and are mixed with 650 g of gum base prepared by cooling the natural gum (Jelutong) to −10° C., grinding it in a mechanical mill, and adding 0.9% guar gum and 0.1% glycerine (w/w). It is mixed in a tumbler and passed through a sieve at 50 mesh. The final mix has a weight of 764.5 g.

To the mix 350 g of mannitol, 300 g of glycocoll, 45 g of syloid 254 and 30 g of behenic acid are added. The components are mixed in a tumbler for 20 minutes. The room temperature must be less than 20° C. In the same mixer 75.5 g of aspartame, 80 g of mint aroma and 25 g of magnesium stearate are added. The components are then mixed for 5 minutes, passed through a sieve at 50 mesh and compressed in a RONCHI rotary press. Theoretical yield is 1670 g. 900 tablets of 1.85 g containing 25 mg of dimenhydrate are obtained.

What is claimed is:

1. A process for the preparation of medicated chewing gum comprising
   (a) forming an inclusion complex of one or more active agents within cyclodextrin,
   (b) drying the inclusion complexes of step (a),
   (c) mixing the dried inclusion complexes with a granulated gum base and and at least one excipient in the absence of added water or organic solvents under a temperature of below 20° C. and a maximum relative humidity of 50%, and
   (d) cold-pressing the mixture of step (c) under a temperature of below 20° C. and a maximum relative humidity of 50% to produce a tablet of medicated chewing gum.

2. The process of claim 1, wherein said β-cyclodextrin is a crystalline β-cyclodextrin with purity greater than 98%.

3. The process of claim 1, wherein the inclusion of the active agent in the cyclodextrin is carried out by suspending the cyclodextrine in distilled water, homogenizing the suspension by stirring, adding the active agent, mixing until inclusion is completed, removing the water mechanically or by heating, and grinding the resultant powder to obtain a dried blend.

4. The process of claim 1, wherein the gum base comprises natural gum, guar gum and glycerine.

5. The process of claim 1, wherein the excipients comprise carbohydrates.

6. The process of claim 5, wherein the excipients comprise at least one of glucose and sucrose.

7. The process of claim 1, wherein the excipients include non-cavity generating compounds.

8. The process of claim 1, wherein the excipients include sweeteners.

9. The process of claim 7, wherein the non-cavity generating compounds include at least one of mannitol, sorbitol and glycine.

10. The process of claim 8, wherein the sweeteners include at least one of aspartame, cyclohexyl sulfamate, saccharin, acesulfame-k, glycyrrhizinate and sterioside.

11. The process of claim 1, wherein the excipients include compression adjuvants.

12. The process of claim 11, wherein the compression adjuvants include at least one of silicon dioxide, magnesium stearate, calcium stearate, behenic acid.

13. The process of claim 1, wherein the active agent comprises l-ascorbic acid.

14. The process of claim 1, wherein the active agent comprises acetaminophen.

15. The process of claim 1, wherein the active agent comprises ibuprofen.

16. The process of claim 1, wherein the active agent comprises dimenhydrinate.

17. The process of claim 1, wherein the active agent comprises chlorhexidine diacetate.

18. The process of claim 1, wherein the active agent comprises nicotine.

19. The process of claim 1, wherein the active agent comprises ginseng.

20. The process of claim 1, wherein the active agent comprises ginkgo biloba extract.

21. The process of claim 1, wherein the active agent comprises tea extract.

22. The process of claim 1, wherein the active agent comprises chromo poly picolinate.

23. A medicated chewing gum tablet produced in accordance with the process of claim 1.

24. A medicated chewing gum tablet produced in accordance with the process of claim 2.

25. A medicated chewing gum tablet produced in accordance with the process of claim 4.

26. A medicated chewing gum tablet produced in accordance with the process of claim 5.

27. A medicated chewing gum tablet produced in accordance with the process of claim 6.

28. A medicated chewing gum tablet produced in accordance with the process of claim 7.

29. A medicated chewing gum tablet produced in accordance with the process of claim 8.

30. A medicated chewing gum tablet produced in accordance with the process of claim 9.

31. A medicated chewing gum tablet produced in accordance with the process of claim 10.

32. A medicated chewing gum tablet produced in accordance with the process of claim 11.

33. A medicated chewing gum tablet produced in accordance with the process of claim 12.

34. A medicated chewing gum tablet produced in accordance with the process of claim 13.

35. A medicated chewing gum tablet produced in accordance with the process of claim 14.

36. A medicated chewing gum tablet produced in accordance with the process of claim 15.

37. A medicated chewing gum tablet produced in accordance with the process of claim 16.

38. A medicated chewing gum tablet produced in accordance with the process of claim 17.

39. A medicated chewing gum tablet produced in accordance with the process of claim 18.

40. A medicated chewing gum tablet produced in accordance with the process of claim 19.

41. A medicated chewing gum tablet produced in accordance with the process of claim 20.

42. A medicated chewing gum tablet produced in accordance with the process of claim 21.

43. A medicated chewing gum tablet produced in accordance with the process of claim 22.

44. The process of claim 1, wherein said cyclodextrin is β-cyclodextrin.

* * * * *